United States Patent
Angold et al.

(10) Patent No.: US 10,154,937 B2
(45) Date of Patent: Dec. 18, 2018

(54) GAIT ORTHOTIC DEVICE AND METHOD FOR PROTECTING GAIT ORTHOTIC DEVICE AND USER FROM DAMAGE

(71) Applicant: Ekso Bionics, Inc., Richmond, CA (US)

(72) Inventors: Russdon Angold, American Canyon, CA (US); Reuben Sandler, Berkeley, CA (US); Robert Moore, Union City, CA (US)

(73) Assignee: Ekso Bionics, Inc., Richmond, CA (US)

( * ) Notice: Subject to any disclaimer, the term of this patent is extended or adjusted under 35 U.S.C. 154(b) by 525 days.

(21) Appl. No.: 14/774,556

(22) PCT Filed: Mar. 12, 2014

(86) PCT No.: PCT/US2014/023987
§ 371 (c)(1),
(2) Date: Sep. 10, 2015

(87) PCT Pub. No.: WO2014/164974
PCT Pub. Date: Oct. 9, 2014

(65) Prior Publication Data
US 2016/0030272 A1    Feb. 4, 2016

Related U.S. Application Data

(60) Provisional application No. 61/779,684, filed on Mar. 13, 2013.

(51) Int. Cl.
G05B 19/04    (2006.01)
A61H 3/00    (2006.01)
(Continued)

(52) U.S. Cl.
CPC .............. *A61H 3/00* (2013.01); *A61F 2/70* (2013.01); *A61H 1/024* (2013.01); *A61H 1/0244* (2013.01);
(Continued)

(58) Field of Classification Search
CPC ........ A61H 3/00; A61H 1/024; A61H 1/0244; A61H 2201/0103; A61H 2201/0173;
(Continued)

(56) References Cited

U.S. PATENT DOCUMENTS

| 4,169,467 A | 10/1979 | Rabischong et al. |
| 4,685,151 A | 8/1987 | Kincheloe |

(Continued)

FOREIGN PATENT DOCUMENTS

| CN | 101204347 | 6/2008 |
| JP | 2000317002 | 11/2000 |

(Continued)

*Primary Examiner* — Glenn Richman
(74) *Attorney, Agent, or Firm* — Diederiks & Whitelaw, PLC

(57) ABSTRACT

A gait orthotic device, such as a powered exoskeleton, includes at least one joint; at least one actuator configured to cause movement of the device at the joint; a cushioning mechanism coupled to the device for absorbing energy or spreading a force during an impact with a surface or object; and a controller. The controller is configured to determine when a fall is occurring and direct the actuator to: orient the device so the cushioning mechanism makes contact with the surface or object during the fall; or reduce a kinetic energy of the device during the fall by performing positive joint work. The cushioning mechanism can take various forms, including an airbag, a spring, a bumper, a roll bar or a kickstand. Preferably, the cushioning mechanism is an airbag in the form of an airbag module that is detachably coupled to the device for removal and replacement.

20 Claims, 3 Drawing Sheets

(51) Int. Cl.
  *A61H 1/02* (2006.01)
  *A61F 2/70* (2006.01)
  *A61F 5/01* (2006.01)

(52) U.S. Cl.
  CPC . *A61F 2002/701* (2013.01); *A61F 2005/0183* (2013.01); *A61H 2201/0103* (2013.01); *A61H 2201/0173* (2013.01); *A61H 2201/5061* (2013.01); *A61H 2201/5069* (2013.01); *A61H 2201/5084* (2013.01); *A61H 2230/625* (2013.01); *A61H 2230/805* (2013.01)

(58) Field of Classification Search
  CPC .... A61H 2201/5061; A61H 2201/5069; A61H 2201/5084; A61H 2230/625; A61H 2230/8057; A61H 2002/701; A61F 2005/0183; A61F 2/70; A61F 2002/701
  See application file for complete search history.

(56) References Cited

U.S. PATENT DOCUMENTS

| | | |
|---|---|---|
| 5,091,992 A | 3/1992 | Pusic |
| 5,558,627 A | 9/1996 | Singer et al. |
| 5,717,996 A | 2/1998 | Feldmann |
| 6,032,299 A | 3/2000 | Welsh |
| 7,150,048 B2 | 12/2006 | Buckman |
| 8,348,875 B2 | 1/2013 | Goffer et al. |
| 8,554,370 B2 | 10/2013 | Goswami et al. |
| 8,880,221 B2 | 11/2014 | Lee et al. |
| 9,649,243 B2 * | 5/2017 | Johnson .................. A61H 3/04 |
| 2007/0010378 A1 | 1/2007 | Katoh et al. |
| 2010/0057253 A1 | 3/2010 | Kwon et al. |
| 2012/0101415 A1 | 4/2012 | Goffer et al. |
| 2014/0005577 A1 * | 1/2014 | Goffer .................. A61H 1/0262 601/34 |

FOREIGN PATENT DOCUMENTS

| | | |
|---|---|---|
| JP | 2007260389 | 10/2007 |
| JP | 2008093762 | 4/2008 |
| JP | 2008104872 | 5/2008 |
| WO | WO 2005/110133 | 11/2005 |
| WO | WO 2012/104833 | 9/2012 |
| WO | WO 2012/002092 | 1/2014 |

* cited by examiner

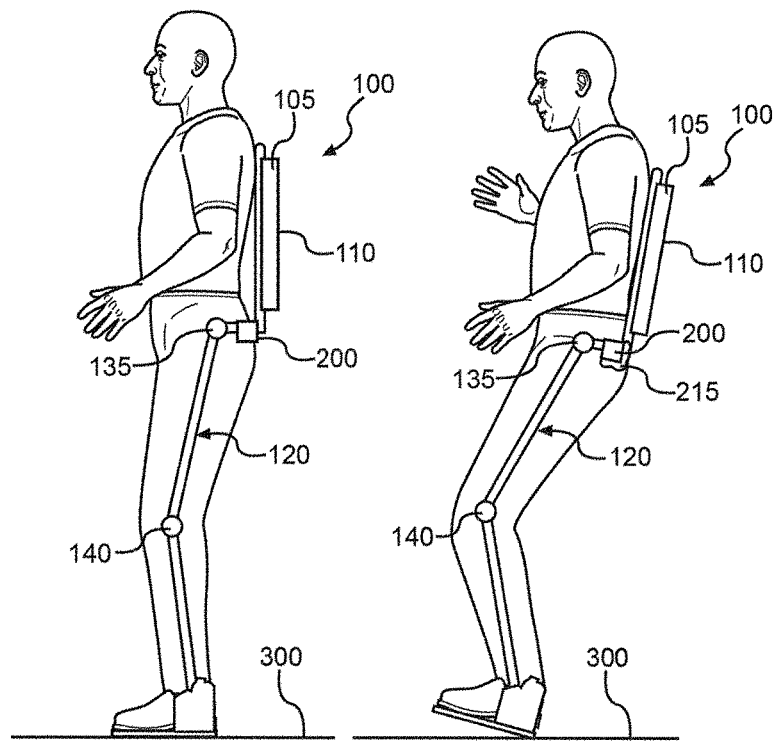
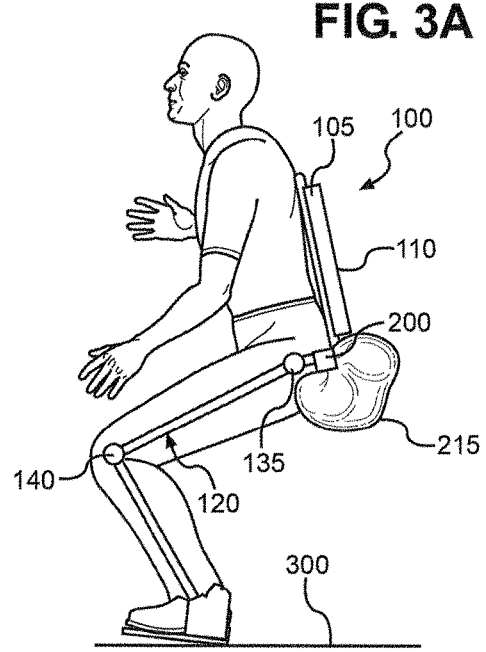
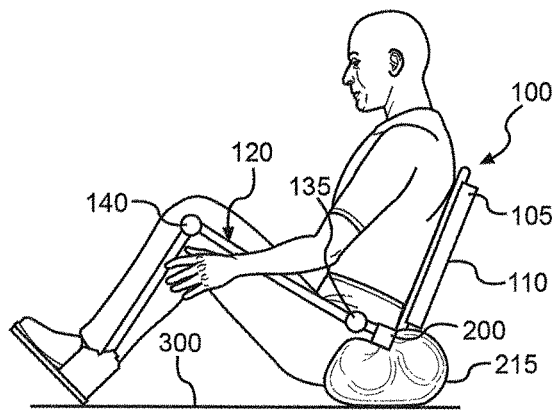
FIG. 3A
FIG. 3B
FIG. 3C
FIG. 3D

GAIT ORTHOTIC DEVICE AND METHOD FOR PROTECTING GAIT ORTHOTIC DEVICE AND USER FROM DAMAGE

CROSS REFERENCE TO RELATED APPLICATIONS

The present application represents a National Stage application of PCT/US2014/023987 entitled "Gait Orthotic Device and Method for Protecting Gait Orthotic Device and User from Damage" filed Mar. 12, 2014, pending, which claims the benefit of U.S. Provisional Patent Application Ser. No. 61/779,684 entitled "Protecting Gait Orthotic Devices and Users from Damage" filed Mar. 13, 2013. The entire content of these applications is incorporated herein by reference.

BACKGROUND OF THE INVENTION

The present invention pertains to gait orthotic devices and, more particularly, to gait orthotic devices that protect the device and a user thereof from damage during a fall.

Powered and unpowered gait orthotic devices have been developed that allow people with mobility disorders to walk and perform tasks that are difficult to accomplish from a wheelchair. One of the primary risks of using such a device is the possibility of a fall that causes an impact with the ground or some other object, thereby resulting in damage to the device or a user of the device. In addition, damage to the device may produce future unpredictable performance. With the above in mind, there is considered to be a need in the art for a gait orthotic device, particularly a powered exoskeleton device, that eliminates or mitigates these problems by protecting the device and a user thereof from damage during a fall.

SUMMARY OF THE INVENTION

The present invention is directed to a gait orthotic device, such as a powered exoskeleton, including: a joint; an actuator configured to cause movement of the device at the joint; a cushioning mechanism coupled to the device and configured to absorb energy or spread a force during an impact with a surface or object; and a controller. The controller is configured to determine when a fall is occurring and direct the actuator to: orient the device so that the cushioning mechanism makes contact with the surface or object during the fall; and/or reduce a kinetic energy of the device during the fall by performing positive joint work.

The cushioning mechanism can take various forms, including an airbag, a spring, a bumper, a roll bar or a kickstand. In one preferred embodiment, the cushioning mechanism is an airbag in the form of an airbag module that is detachably coupled to the device such that the airbag module can be removed and replaced. The airbag module is coupled to the device at a position adjacent to the user's head, pelvis, hips or knees. The airbag module includes a compressed air canister, a canister puncturing mechanism configured to puncture the compressed air canister, a trigger mechanism configured to actuate the canister puncturing mechanism, a folded, flexible bag configured to receive air from the compressed air canister, and a mounting component configured to detachably couple the airbag module to the gait orthotic device. In one particularly preferred embodiment, the device includes a plurality of airbag modules and the controller is further configured to selectively deploy one or more of the airbag modules during a fall, with the selection being based on a position of the device during the fall or a sensed direction in which the device is falling.

Additional objects, features and advantages of the invention will become more readily apparent from the following detailed description of preferred embodiments thereof when taken in conjunction with the drawings wherein like reference numerals refer to common parts in the several views.

BRIEF DESCRIPTION OF THE DRAWINGS

FIGS. 3A-D are illustrations showing the gait orthotic device and airbag module during a fall.

DETAILED DESCRIPTION OF THE PREFERRED EMBODIMENTS

Detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

The present invention provides a system and methods for protecting a gait orthotic device, particularly a powered exoskeleton device, and a user of the device from damage and injury when a fall occurs. Three categories of protection methods are described that provide maximum benefit when used in concert, although they can also be used independently to provide varying degrees of protection. The first category of protection methods absorbs energy and spreads applied forces during an impact by means of cushioning, such methods being referred to as "cushioning methods". The second category of protection methods absorbs energy during the fall prior to impact by having the device perform positive joint work, such methods being referred to as "joint work methods". The third category of protection methods relies on a hybrid response, using joint work to actively position the system during the fall to maximize the effectiveness of the cushioning methods or minimize the exposure of the device and user to damage, such methods being referred to as "positioning methods".

In general, there are two types of gait orthotic devices: powered and unpowered. One type of powered device, and the type of device for use with the present invention, is a powered exoskeleton. A common type of unpowered device is a reciprocating gait orthosis. Powered devices have at least one joint on each side of the body that has the ability to apply a torque about the joint in order to perform positive and negative joint work. In contrast, unpowered devices do not have the ability to perform positive joint work without input from the user's body. As a result, while unpowered devices can employ, at best, cushioning protection methods, powered devices can employ all three categories of protection methods as discussed in detail below.

Figure 1:
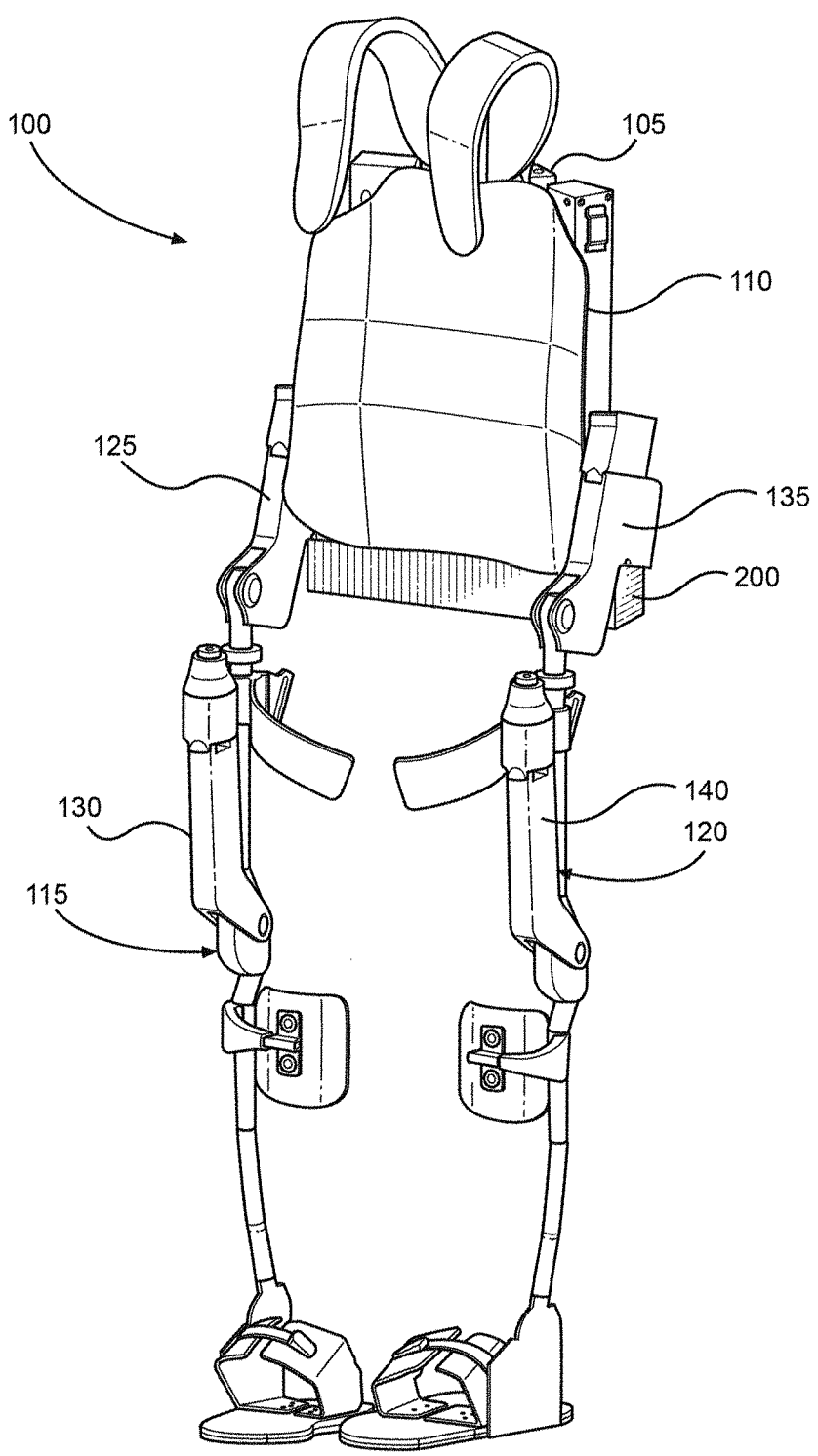
FIG. 1 is a perspective view of a gait orthotic device in accordance with the present invention.

With reference now to FIG. 1, there is shown a gait orthotic device constructed in accordance with the present invention. Specifically, the gait orthotic device is in the form of a powered exoskeleton 100 that includes a controller 105

(or control system), a torso 110, a right leg 115 and a left leg 120. Right and left legs 115, 120 have actuated knees and hips. In particular, right leg 115 has a hip actuator 125 and a knee actuator 130, while left leg 120 has a hip actuator 135 and a knee actuator 140. In use, an exoskeleton user would wear exoskeleton 100 with torso 110 coupled to the user's torso, right leg 115 coupled to the user's right leg and left leg 120 coupled to the user's left leg. Controller 105 controls the motion of exoskeleton 100 through actuators 125, 130, 135, 140 based on various signals received from sensors (not shown), as known in the art, so that the user is able to walk.

For use on a gait orthotic device such as exoskeleton 100, numerous cushioning method concepts were generated and systematically evaluated to determine the embodiment that best met the following qualifications: does not hinder normal performance; is repeatable and predictable; deploys quickly enough to provide protection; stabilizes and provides protection for the neck; protects the hips; prevents broken bones; is aesthetically pleasing; and is safe for a spotter to use. Five general embodiments of cushioning mechanisms were considered:

1. Passive Bumpers. Cushioning bumpers are placed at critical locations around the device.
2. Passive Bow Springs. Large, flexible hoops are positioned around the device so that they make contact first during a fall and reduce the magnitude of the impact.
3. Active Expanding Bumpers. These bumpers unfurl during a fall and can therefore be larger than the passive bumpers in order to absorb more energy.
4. Airbags. Gas-filled bags are inflated during a fall and absorb energy on impact. Because falls take hundreds of milliseconds, it is possible to fill the bags from a compressed gas canister (e.g., compressed $CO_2$ canister) as well as from the explosive reactions that are used in automotive airbags.
5. Kickstands. The device releases a prop in the direction of the fall to prevent the device from hitting the ground altogether, such as a telescoping, spring biased or fluid regulated prop.

Based on an evaluation of these cushioning mechanisms, it was determined that the preferred cushioning method is to use airbags, although each embodiment is usable in connection with the present invention.

For the purposes of this discussion, the term "airbag" refers to a flexible container (i.e., bag) that can be packaged in a small volume and selectively filled with a larger volume of gas, which is stored in a compressed state within a sealed container. When the airbag needs to perform as a cushion, the compressed gas is allowed to move from the sealed container to the bag. This gas transfer increases the pressure inside the bag and causes it to expand to a larger volume. The inflated bag can be oriented between the device and an impact surface to absorb energy and spread the applied forces. The cushioning effect of the airbag is the result of three properties of the airbag: gas is a relatively soft spring that can absorb energy through compression; the expanded bag creates a relatively large area in contact with the impact surface that decreases the forces on the device; and gas outflow from the inflated bag during impact can act as a damper to prevent rebound.

In certain embodiments, airbags are provided on all sides of exoskeleton 100. This protects exoskeleton 100 well since falls can occur in any direction. In a preferred embodiment, small modular airbags are located at likely impact points, such as the head, pelvis, hips and knees. By using onboard sensors, controller 105 can detect a position and direction of exoskeleton 100 as it falls and selectively deploy the ideal airbags prior to impact. This strategy minimizes the amount of compressed air needed to protect the device and user, facilitates mounting of the airbags on the device without interfering with its primary function, and minimizes the cost and effort involved in replacing discharged airbags.

Figure 2:
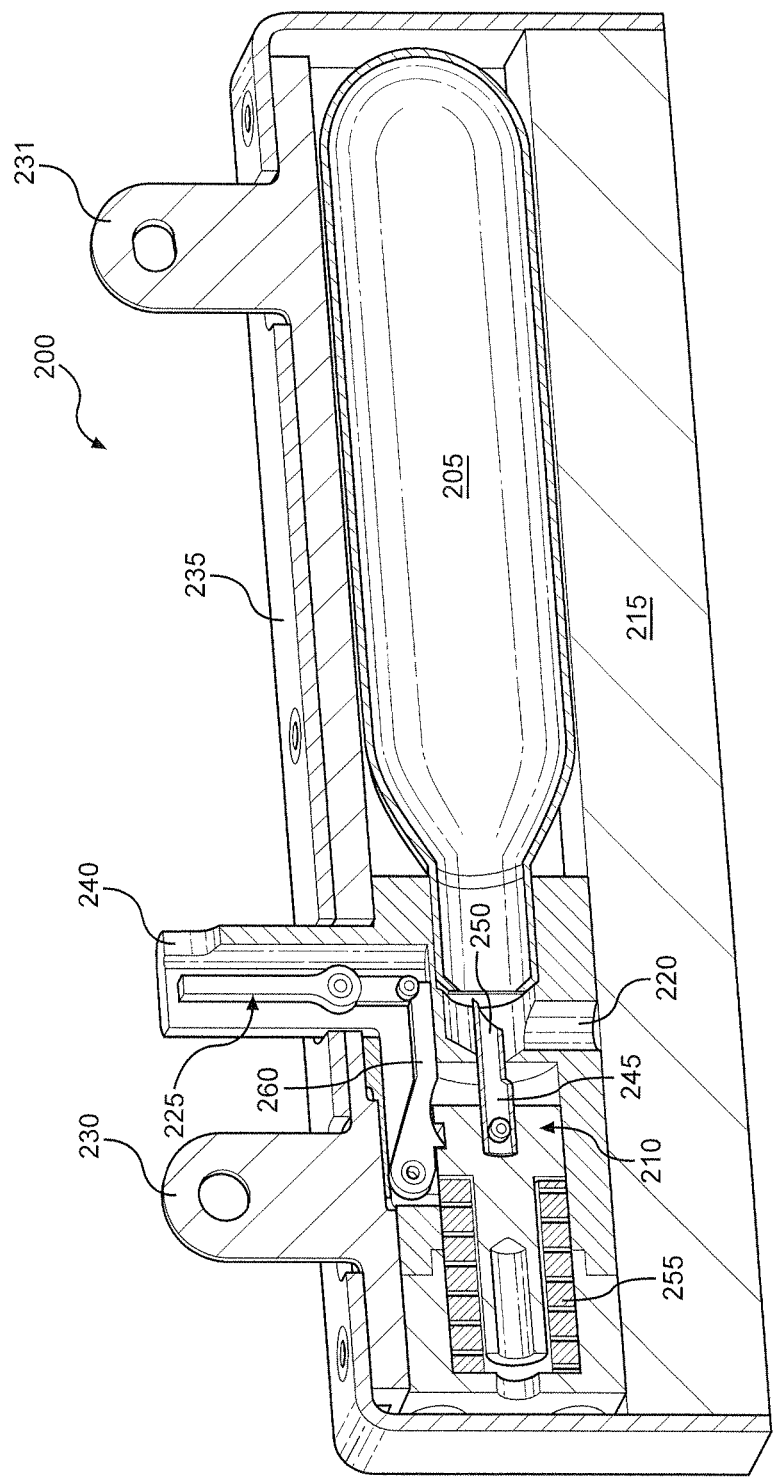
FIG. 2 is a perspective, cross-sectional view of an airbag module for the gait orthotic device.

Preferably, each airbag is a module that can be removed after deployment and replaced with a factory-repackaged unit by the user. With specific with reference to FIG. 2, there is shown an airbag module 200 for use with a gait orthotic device, such as exoskeleton 100. Airbag module 200 mainly includes: a compressed air canister 205; a component (not shown) that mounts and secures the canister; a canister puncturing mechanism 210; a folded flexible bag 215 exposed to a component 220 that allows air to move between punctured canister 205 and bag 215; a trigger mechanism 225 that causes puncturing mechanism 210 to operate; mounting components 230, 231 to allow rigid and accurate connection to exoskeleton 100; a housing 235 to enclose and protect the various components; a flap or cover (not shown) that allows the airbag to expand outside of module and be positioned between the device and an impact surface; and a component 240 that covers trigger mechanism 225 to prevent undesired deployment. A portion 245 of the puncturing mechanism that enters canister 205 is sharp to minimize the time and force required to access the compressed air inside canister 205. Additionally, puncturing mechanism 210 is cylindrical and has a centrally located channel 250, which allows air to move from canister 205 to packaged bag 215. Sharp portion 245 of puncturing mechanism 210 is stored in a position such that, when it is unlocked by trigger mechanism 225, the potential energy in a compressed coil spring 255 is converted to a large kinetic energy directed towards the canister seal. Trigger mechanism 225 holds puncture mechanism 210 in place through a pivoting lever 260 that is preferably biased in a locked position by another spring (not shown).

When airbag module 200 is not installed in exoskeleton 100, it is impossible to accidentally, and difficult to intentionally, deploy airbag module 200. When installed on exoskeleton 100, component 240 covers trigger mechanism 225 except for at an opening (shown but not separately labeled in FIG. 2) and sensors on exoskeleton 100 detect whether: mounting components 230, 231 of airbag module 200 are present and properly located; pins connecting module 200 to exoskeleton 100 are present; and trigger mechanism 225 is locked. A trigger actuator (not shown), such as a solenoid, is mounted on exoskeleton 100 so that, when provided the correct voltage or current, it overpowers a spring holding it in a retracted state and releases trigger mechanism 225. An additional sensor ensures that the trigger actuator is in the retracted state before allowing exoskeleton 100 to operate.

In one embodiment, the number of airbag modules 200 used to provide the desired level of protection can be reduced by also employing positioning methods that work in concert with the airbag cushioning methods. This strategy involves initiating and coordinating device joint work (i.e., pivotal movement at the joints) during a fall to increase the likelihood that the position of exoskeleton 100 at impact allows for optimal cushioning using the installed airbag modules 200. The control strategy uses the position and direction of exoskeleton 100 and the known locations and presence of airbag modules 200 to determine and direct exoskeleton 100 into the ideal impact orientation. For example, in a backwards fall from standing, the user's head is at risk of impacting the ground but, rather than providing airbag module 200 near the head, exoskeleton 100 can flex at the hips and knees to keep the torso and head close to upright and direct the impact to the pelvis region. Thus, an ideal location for airbag module 200 is behind the user's pelvis (as shown in FIGS. 3A-D and discussed below). Similarly, in a sideways fall, exoskeleton 100 can be reoriented so that the impact is again directed to airbag module 200 behind the user's pelvis.

At the point, when a fall is imminent, the height and mass of the system (i.e., the combination of the device and user) provides a potential energy that, if not attenuated, will be converted to an equal amount of kinetic energy just before impact. The risk of damage to the device and user is directly related to the amount of kinetic energy at impact. In one embodiment, the user and exoskeleton 100 are protected during a fall by controlling exoskeleton 100 to resist the conversion of potential energy into kinetic energy by actuating the powered joints during descent (i.e., using actuators 125, 130, 135, 140 to cause pivotal movement at the joints). This actuation results in positive joint work, which slows the downward acceleration. In other words, exoskeleton 100 controls the fall in a manner analogous to an able-bodied person slowly squatting from a standing to sitting position on the ground rather than simply letting himself/herself fall.

Turning to FIGS. 3A-D, exoskeleton 100 is shown during a backwards fall. In FIG. 3A, the user and exoskeleton 100 are shown standing normally on the ground 300. In FIG. 3B, the user begins to fall backwards. Exoskeleton 100 detects the fall using sensors (such as weight, tilt, orientation or inertia sensors not shown) and controller 105. In order to mitigate any damage caused by the fall, exoskeleton 100 employs at least one of the cushioning, positioning and joint work methods described above, the actions of which are shown in FIGS. 3B-D. Specifically, in a preferred form, bag 215 of airbag module 200 is deployed to absorb the energy of the fall and spread the forces that occur during an impact with the ground 300 (cushioning methods). Additionally, actuators 125, 130, 135, 140 work to both position exoskeleton 100 such that it is bag 215 that impacts the ground 300 (positioning methods) and also slow the fall by reducing kinetic energy through positive joint work (joint work methods).

For powered devices such as exoskeleton 100, a preferred embodiment of airbag module 200 includes no electronics inside housing 235. The operation of module 200 is instead completely controlled by controller 105 of exoskeleton 100. This simplifies the design of airbag module 200 and reduces cost by leveraging the electronics and control elements already present in exoskeleton 100. However, it is also possible to have airbag module 200 include electronics and a power supply inside module 200 such that the operation of module 200 is directly controlled by the module. On such devices, airbag modules 200 can also have sensing capabilities that detect orientations and inertias to determine when to deploy the airbag, while communicating with the actuator controller for exoskeleton 100.

A preferred characteristic of airbag module 200 and the triggering thereof is that it is failsafe. This means that, if a component in module 200 or an external triggering apparatus fails, exoskeleton 100 is still protected. Thus, in one embodiment, a component failure results in airbag module 200 deploying so that the user is aware of the compromised elements. Alternatively, a warning is communicated to the user regarding the failure.

It should be readily apparent that, while the present invention is primarily directed to the use of airbags as a method for reducing injury to the user and device during falls, any of the cushioning mechanisms mentioned above can be employed. For example, during a backwards fall such as the one shown in FIG. 3, the device can simply have bumpers on the bottom of the torso, with the device being oriented during the fall so that the bumpers impact first. Or, in other embodiments, the device can have deployable roll bars that unfold around the user when the device detects a fall. In such an embodiment, the controller similarly positions the device so that a fall results in an impact on the roll bars. For instance, if the fall is to the side and the roll bars are located in the rear, the device controller can kick one of the device legs so that the device rotates and the deployed roll bars impact first, even if kicking one of the legs increases the overall kinetic energy of the device, something that, as noted above, is not generally desirable.

Based on the above, it should be readily apparent that the present invention provides for a gait orthotic device that protects the device and a user thereof from damage during a fall. Although described with reference to preferred embodiments, it should be readily understood that various changes or modifications could be made to the invention without departing from the spirit thereof. For example, the present invention is usable in a broad range of gait orthotic devices, both powered and unpowered. Additionally, various combinations of cushioning, positioning and joint work methods, and the different embodiments thereof, can be used together. In general, the invention is only intended to be limited by the scope of the following claims.

The invention claimed is:

1. A powered exoskeleton configured to be coupled to a user and including a plurality of joints comprising:
   right leg, left leg and torso portions configured to be coupled to the user and interconnected through a plurality of joints;
   a plurality of actuators configured to cause movement of the powered exoskeleton through the plurality of joints;
   a cushioning mechanism coupled to the powered exoskeleton and configured to absorb energy or spread a force during an impact with a surface or object; and
   a controller configured to determine when a fall is occurring and direct at least one of the plurality of actuators to:
      orient the powered exoskeleton so that the cushioning mechanism makes contact with the surface or object during the fall; or
      reduce a kinetic energy of the powered exoskeleton during the fall.

2. The powered exoskeleton of claim 1, wherein the cushioning mechanism is an airbag, a spring, a bumper, a roll bar or a kickstand.

3. The powered exoskeleton of claim 1, wherein the cushioning mechanism is an airbag, the airbag constituting an airbag module that is detachably coupled to the powered exoskeleton such that the airbag module can be removed and replaced, and further wherein the airbag module is coupled to the powered exoskeleton at a position adjacent to a user's head, pelvis, hips or knees.

4. The powered exoskeleton of claim 3, wherein the powered exoskeleton includes a plurality of airbag modules and the controller is further configured to selectively deploy one or more of the plurality of airbag modules during the fall.

5. The powered exoskeleton of claim 4, wherein the controller selects the one or more of the plurality of airbag modules based on a position of the powered exoskeleton during the fall or a direction in which the powered exoskeleton is falling.

6. The powered exoskeleton of claim 3, wherein the airbag module includes:
a compressed air canister;
a canister puncturing mechanism configured to puncture the compressed air canister;
a trigger mechanism configured to actuate the canister puncturing mechanism;
a folded, flexible bag configured to receive air from the compressed air canister; and
a mounting component configured to detachably couple the airbag module to the powered exoskeleton.

7. The powered exoskeleton of claim 1, wherein the controller is configured to direct the actuator to reduce the kinetic energy of the powered exoskeleton by performing positive joint work.

8. A gait orthotic device configured to be coupled to a user and comprising:
an actuator configured to cause movement of the gait orthotic device at a joint;
a cushioning mechanism coupled to the gait orthotic device and configured to absorb energy or spread a force during an impact with a surface or object; and
a controller configured to determine when a fall is occurring and direct the actuator to:
orient the gait orthotic device so that the cushioning mechanism makes contact with the surface or object during the fall; or
reduce a kinetic energy of the gait orthotic device during the fall.

9. The gait orthotic device of claim 8, wherein the cushioning mechanism is an airbag, a spring, a bumper, a roll bar or a kickstand.

10. The gait orthotic device of claim 8, wherein the cushioning mechanism is an airbag, the airbag constituting an airbag module that is detachably coupled to the gait orthotic device such that the airbag module can be removed and replaced, and further wherein the airbag module is coupled to the gait orthotic device at a position adjacent to a user's head, pelvis, hips or knees.

11. The gait orthotic device of claim 10, wherein the gait orthotic device includes a plurality of airbag modules and the controller is further configured to selectively deploy one or more of the plurality of airbag modules during the fall.

12. The gait orthotic device of claim 11, wherein the controller selects the one or more of the plurality of airbag modules based on a position of the gait orthotic device during the fall or a direction in which the gait orthotic device is falling.

13. The gait orthotic device of claim 10, wherein the airbag module includes:
a compressed air canister;
a canister puncturing mechanism configured to puncture the compressed air canister;
a trigger mechanism configured to actuate the canister puncturing mechanism;
a folded, flexible bag configured to receive air from the compressed air canister; and
a mounting component configured to detachably couple the airbag module to the gait orthotic device.

14. The gait orthotic device of claim 8, wherein the controller is configured to direct the actuator to reduce the kinetic energy of the gait orthotic device by performing positive joint work.

15. A method for protecting a gait orthotic device configured to be coupled to a user, including various joints, actuators configured to cause movement of the gait orthotic device through the joints, a cushioning mechanism coupled to the gait orthotic device and configured to absorb energy or spread a force during an impact with a surface or object, and a controller, and the user thereof from damage during a fall, the method comprising:
determining, with the controller, when the fall is occurring;
directing, with the controller, at least one of the actuators to:
orient the gait orthotic device so that the cushioning mechanism make contact with the surface or object during the fall; or
reduce a kinetic energy of the gait orthotic device during the fall.

16. The method of claim 15, wherein the cushioning mechanism is an airbag module, the method further comprising:
removing the airbag module if the airbag module deploys an airbag during the fall; and
replacing the airbag module with another airbag module.

17. The method of claim 15, wherein the cushioning mechanism is a plurality of airbag modules, the method further comprising:
selectively deploying one or more of the airbag modules during the fall.

18. The method of claim 17, further comprising:
selecting the one or more of the airbag modules based on a position of the gait orthotic device during the fall or a direction in which the gait orthotic device is falling.

19. The method of claim 15, wherein the cushioning mechanism is an airbag module including a compressed air canister, a canister puncturing mechanism configured to puncture the compressed air canister, a trigger mechanism configured to actuate the canister puncturing mechanism and a folded, flexible bag configured to receive air from the compressed air canister, the method further comprising:
activating the trigger mechanism to actuate the canister puncturing mechanism;
puncturing the compressed air canister; and
directing compressed air from the air canister to expand the bag.

20. The method of claim 15, wherein the at least one of the actuators reduces the kinetic energy of the gait orthotic device by performing positive joint work.

* * * * *